(12) United States Patent
Carson et al.

(10) Patent No.: US 7,094,597 B1
(45) Date of Patent: Aug. 22, 2006

(54) VACCINE COMPOSITIONS AND METHODS USEFUL IN INDUCING IMMUNE PROTECTION AGAINST ARTHRITOGENIC PEPTIDES INVOLVED IN THE PATHOGENESIS OF RHEUMATOID ARTHRITIS

(75) Inventors: Dennis A. Carson, Del Mar, CA (US); Salvatore Albani, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/616,247

(22) Filed: Jul. 14, 2000

Related U.S. Application Data

(60) Division of application No. 09/107,615, filed on Jun. 30, 1998, now Pat. No. 6,153,200, which is a division of application No. 08/618,464, filed on Mar. 15, 1996, now Pat. No. 5,773,570, which is a continuation-in-part of application No. 08/246,988, filed on May 20, 1994, now abandoned.

(51) Int. Cl.
*C12N 15/00* (2006.01)
*C07H 21/04* (2006.01)

(52) U.S. Cl. .................................. 435/320.1; 536/23.7
(58) Field of Classification Search ............. 424/201.1, 424/184.1, 203.1; 514/2, 4
See application file for complete search history.

(56) References Cited

U.S. PATENT DOCUMENTS

| | | | |
|---|---|---|---|
| 4,654,419 A | 3/1987 | Vaughan et al. | |
| 4,683,295 A | 7/1987 | Carson | |
| 4,732,757 A | 3/1988 | Stolle et al. | |
| 5,116,725 A | 5/1992 | Vaughan et al. | |
| 5,310,732 A | 5/1994 | Carson et al. | |
| 5,541,164 A | 7/1996 | Carson et al. | |
| 5,728,385 A | 3/1998 | Classen | |
| 5,773,570 A * | 6/1998 | Carson et al. | 424/201.1 |
| 5,891,435 A | 4/1999 | Muir et al. | |
| 5,922,567 A | 7/1999 | Au-Young et al. | |

FOREIGN PATENT DOCUMENTS

| | | |
|---|---|---|
| WO | WO90/14835 | 12/1990 |
| WO | WO95/31984 | 11/1995 |

OTHER PUBLICATIONS

Marshall. E., "Gene Therapy's Growing Pains", Science, 269:1050-1055, Aug. 1995.*
Miller et al, "Targeted Vectors for Gene Therapy", FASEB J., 9:190-199, 1995.*
NIH Report "Report and Recommendation of the Panel to Assess NIH Invetment in Gene Therapy Reseach", Dec. 1995.*
Bardwell et al., The Journal of Biological Chemistry, vol. 261, No. 4, pp. 1782-1785, 1986.*
GenCore Accession # HHECDJ.*

Albani, S., et al., "Positive Selection in Autoimmunity: Abnormal Immune Responses to a Bacterial dnaJ Antigen Determinant in Patients with Early Rheumatoid Arthritis," *Nature Medicine*, vol. 1, No. 5, pp. 448-452, 1995.
Bonnin, D., et al., "MHC-Derived Peptides Drive Positive T Cell Selection in the Thymus: from a Physiological System to an HLA DRB1*0401 Transgenic Mouse Model for Rheumatoid Arthritis?", *Arthritis and Rheumatism*, vol. 39, No. 9 Suppl., p. S160, Oct. 1996.
Auger, I., et al., "HLA-DR4 and HLA-DR10 Motifs that Carry Susceptibility to Rheumatoid Arthritis Bind 70-kD Heat Shock Proteins," *Nature Medicine*, vol. 2, No. 3, pp. 306-310, Mar. 1996.
Albani, et al., "Genetics and Environmental Factors in the Immune Pathogenesis of Rheumatoid Arthritis," *Rheumatic Disease Clinics of North America*, 18/4:729-740, 1992.
Stastney, P., et al., "Immunogenetics of Rheumatoid Arthritis and Juvenile Arthritis", *Recenti Progressi in Medicina*, vol. 82, No. 7-8, pp. 409-416, 1991.
Nepom, G., "Prediction of Susceptibility to Rheumatoid Arthritis by Human Leukocyte Antigen Genotying" *Rheumatic Disease Clinics of North America*, vol. 18, No. 4, pp. 785-792, Nov. 1992.
Weyand, C., et al., "The Influence of HLA-DRB1 Genes on Disease Severity in Rheumatoid Arthritis," Annals of Internal Medicine, vol. 117, No. 10, pp. 801-806, Nov. 15, 1992.
Fairchild, P., et al., "Peptide-MHC Interaction in Autoimmunity," *Current Opinion in Immunology*, vol. 4, pp. 748-753, 1992.
Life, P.F., et al., "Synovial Fluid Antigen-Presenting Cells Unmask Peripheral Blood T Cell Responses to Bacterial Antigens in Inflammatory Arthritis," *Clin. Exp. Immunol.* vol. 79, pp. 189-194, 1990.
Van Den Broek, M.F., et al., "Protection Against Streptococcal Cell Wall-Induced Arthritis by Pretreatment with the 65-kD Mycobacterial Heat Shock Protein," *J. Exp. Med.*, vol. 170, pp. 449-466, Aug. 1989.
Anderton, S.M., et al. "Activation of T Cells Recognizing Self 60-kD Heat Shock Protein Can Protect Against Experimental Arthritis," *J. Exp. Med.*, vol. 181, pp. 943-952, Mar. 1995.
Albani, S., et al., "A Multistep Molecular Mimicry Hypothesis for the Pathogenesis of Rheumatoid Arthritis," *Immunology Today*, vol. 17, No. 10, pp. 466-470, Oct. 1996.

(Continued)

*Primary Examiner*—Patricia A. Duffy
(74) *Attorney, Agent, or Firm*—DLA Piper Rudnick Gray Cary US LLP

(57) ABSTRACT

Vaccine compositions useful in inducing immune protection in a host against arthritogenic peptides involved in the pathogenesis of rheumatoid arthritis are disclosed. Each vaccine composition provides antigenic dnaJp1 peptide (by including the peptide or a polynucleotide which encodes the peptide) and, optionally, other peptide fragments of the microbial dnaJ protein and/or human homologs thereof. Methods for identifying persons who are predisposed to develop rheumatoid arthritis and methods for use of the inventive vaccines are also disclosed.

5 Claims, 5 Drawing Sheets

OTHER PUBLICATIONS

Anderton et al, "Differential Mycrobacterial 65-kDa Heat Shock Protein T Cell Epitope Recognition after Adjuvant Arthritis-Inducing or Protective Immunization Protocols[1]," *J. Immunology* 152:3656-64, 1994.

Albani et al, "HLA Binding Studies Support a Role for the QKRAA Susceptibility Sequence to Rheumatoid Arthritis (RA) in Positive Selection and Activation of Pathogenic T Lymphocytes," *Arthritis and Rheumatism*, 38/9 Suppl., p. S181, Abstract#173, 1995.

Plotkin, S.A., et al., "New Technologies for Making Vaccines," *Vaccines*, pp. 568-575, 1988.

Albani, S., et al., "Molecular Basis for the Association Between HLA DR4 and Rheumatoid Arthritis. From the Shared Epitope Hypothesis to a Peptidic Model of Rheumatoid Arthritis," *Clin. Biochem.* vol. 25, pp. 209-212, 1992.

La Cava, A., et al., "The QKRAA Disease Susceptibility Sequence for Rheumatoid Arthritis (RA) is a B Cell Epitope Shared by the Epstein-Barr Virus (EBV) Protein gp110 and the *E. coli* Heat Shock Protein dnaJ Possible Implications for Disease Pathogenesis," *Arthritis & Rheum.* 36(9) Suppl. pp. S127 Abstract 1993.

Asseldonk, M., et al., "Cloning, Nucleotide Sequence, and Regulatory Analysis of the *Lactococcus lactis* dnaJ Gene,", *Journal of Bacteriology*, 175(6), pp. 1637-1644, Mar. 1993.

Bardwell, J.C.A., et al., "The Nucleotide Sequence of the *Escherichia coli* K12 dnaJ+ Gene," *The Journal of Biological Chemistry*, vol. 261, No. 4, pp. 1782-1785, Feb. 5, 1986.

Ohki, M. et al., "Nucleotide Sequence of the *Escherichia coli* dnaJ Gene and Purification of the Gene Product*", The Journal of Biological Chemistry, vol. 261, No. 4, pp. 1778-1781, 1986.

Albani, S., et al., "The Susceptibility Sequence to Rheumatoid Arthritis in a Cross-Reactive B Cell Epitope Shared by the *Escherichia coli* Heat Shock Protein dnaJ and the Histocompatibility Leukocyte Antigen DRB10401 Molecule," *J. Clin. Invest.*, vol. 89, pp. 327-331, 1992.

van Eden, W., et al., "Cloning of the Mycobacterial Epitope Recognized by T Lymphocytes in Adjuvant Arthritis," *Nature*, vol. 331, pp. 171-173, Jan. 14, 1988.

Silver, P.A., et al. "Eukaryotic DnaJ Homologs and the Specificity of Hsp70 Activity," *Cell*, vol. 74, pp. 5-6, Jul. 16, 1993.

Zuber et al., "Cloning, Sequencing and Expression of the dnaJ gene of *Coxiella burnetii*," *Gene*, vol. 152 pp. 99-102, 1995.

DeGraeff-Meeder, E.R., et al., "Recognition of Human 60kD Heat Shock Protein by Mononuclear Cells from Patients with Juvenile Chronic Arthritis," *The Lancet*, vol. 337, pp. 1368-1372, Jun. 8, 1991.

Brackertz et al, "OM-8980 in Rheumatoid Arthritis: A 6-Month Double Blind Placebo Controlled Multicenter Study," *Journal of Rheumatology*, vol. 16, pp. 19-23, 1989.

Marsh, S.G.E., et al, "HLA Class II Nucleotide Sequences, 1991," *Tissue Antigens*, vol. 37, pp. 181-189, 1991.

Albani, S., et al., "Immune Responses to the *Escherichia coli* dnaJ Heat Shock Protein in Juvenile Rheumatoid Arthritis and their Correlation with Disease Activity," *The Journal of Pediatrics*, vol. 124, No. 4, pp. 561-565, Apr. 1994.

GenCore Accession # HHECDJ.

* cited by examiner

|  | Peptide | | | | |
| --- | --- | --- | --- | --- | --- |
| HLA-DRB1 Type Donor | dnaJp1 | dnaJp2 | dnaJpV | S1 | S6 |
| DRB1*0401 (patient) | 1.07 | 0.16 | 0.04 | 0.09 | 0.19 |
| DRB1*0401 (normal subject) | 1.06 | 0.18 | 0.03 | 0.08 | 0.17 |
| DRB1*0407 (normal subject) | 1.00 | 0.19 | 0.14 | 0.11 | 0.22 |

FIG. 5

```
                            SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 1055 base pairs
        (B) TYPE: nucleic acid
        (C) STRANDEDNESS: single
        (D) TOPOLOGY: linear (ii) MOLECULE TYPE: DNA (clonal)

(vii) IMMEDIATE SOURCE:
        (B) CLONE: E. coli K12 dnaJ polynucleotide (cDNA)

(ix) FEATURE:
        (A) NAME/KEY: CDS
        (B) LOCATION: 1..1054

(xi) SEQUENCE DESCRIPTION: SEQ ID NO: 1:

ATGGCTAAGC AAGATTATTA CGAGATTTTA GGCGTTTCCA AAACAGCGGA AGAGCGTGAA      60

ATCAGAAAGG CCTACAAACG CCTGGCCATG AAATACCACC CGGACCGTAA CCAGGGTGAC     120

AAAGAGGCCT ATGGTCATGC TGCGTTTGAG CAAGGTGGCA TGGGCGGCGG CGGTTTTGGC     180

GGCGGCGCAG ACTTCAGCGA TATTTTTGGT GACGTTTTCG GCGATATTTT TGGCGGCGGA     240

CGTGGTCGTC AACGTGCGGC GCGCGGTGCT GATTTACGCT ATAACATGGA GCTCACCCTC     300

GAAGAAGCTG TACGTGGCGT GACCAAAGAG ATCCGCATTC CGACTCTGGA AGAGTGTGAC     360

GTTTGCCACG GTAGCGGTGC AAAACCAGGT ACACAGCCGC AGACTTGTCC GACCTGTCAT     420

GGTTCTGGTC AGGTGCAGAG GCGCCAGGGA TTCTTCGCTG RACAGCAGAC CTGTCAACAC     480

TGTCAGGGCC GCGGTACGCT GATCAAAGAT CCGTGTAACA AATGTCATGG TCATGGTCGT     540

CTTGAGCGCA GCAAAACGCT TCCGTTAAAA TCCCGGCAGG GGTGGACACT GGACACCGCA     600

TCCGTCTTGC GGGCGAAGGT GAAGCGGGCG AGCATGGCGC ACCGGCAGGC GATCTGTACG     660

TTCAGGTTCA GGTTAAACAG CACCCGATTT TCGAGCGTGA AGGCAACAAC CTGTATTGCG     720

AAGTCCCGAT CAACTTCGCT ATGGCGGCGC TGGGTGGCGA AATCGAAGTA CCGACCCTTG     780

ATGGTCGCGT CAAACTGAAA GTGCCTGGCG AAACCCAGAC CGGTAAGCTA TTCCGTATGC     840

GCGGTAAAGG CGTCAAGTCT GTCCGCGGTG GCGCACAGGG TGATTTGCTG TGCCGCGTTG     900

TCGTCGAAAC ACCGGTAGGC CTGAACGAAA GGCAGAAACA GCTGCTGCAA GAGGTGCAAG     960

AAAGATTCGG TGGCCCAACC GGCGAGCACA ACAGCCCGCG CTCAAAGAGC TTCTTTGATG    1020

GTGTGAAGAA GTTTTTTGAC GACCTGACCC GCTAA                              1055
```

(2) INFORMATION FOR SEQ ID NO: 2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: RA Susceptibility Sequence Variant (ix) FEATURE:
        (A) NAME/KEY: Peptide
        (B) LOCATION: 1..5

(xi) SEQUENCE DESCRIPTION: SEQ ID NO: 2:

Gln Lys Arg Arg Ala
1               5

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: RA Susceptibility Sequence Variant (ix) FEATURE:
        (A) NAME/KEY: Peptide
        (B) LOCATION: 1..5

(xi) SEQUENCE DESCRIPTION: SEQ ID NO: 3:

Gln Arg Arg Ala Ala
1               5

(2) INFORMATION FOR SEQ ID NO: 4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: Immunogenic dnaJ Peptide (ix) FEATURE:
        (A) NAME/KEY: Peptide
        (B) LOCATION: 1..15

(xi) SEQUENCE DESCRIPTION: SEQ ID NO: 4:

Gln Lys Arg Ala Ala Tyr Asp Gln Tyr Gly His Ala Ala Phe Glu
1               5                   10                  15

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: single
        (D) TOPOLOGY: linear

```
    (ii) MOLECULE TYPE: peptide (vii) IMMEDIATE SOURCE:
        (B) CLONE: Immunogenic dnaJ Peptide (ix) FEATURE:
        (A) NAME/KEY: Peptide
        (B) LOCATION: 1..15

(xi) SEQUENCE DESCRIPTION: SEQ ID NO: 5:

Asp Glu Arg Ala Ala Tyr Asp Gln Tyr Gly His Ala Ala Phe Glu
1               5                  10                  15

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: dnaJp2

(ix) FEATURE:
        (A) NAME/KEY: Peptide
        (B) LOCATION: 1..15

(xi) SEQUENCE DESCRIPTION: SEQ ID NO: 6:

Val Leu Thr Asp Ser Gln Lys Arg Ala Ala Tyr Asp Gln Tyr Gly
1               5                  10                  15

(2) INFORMATION FOR SEQ ID NO: 7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: S1

(ix) FEATURE:
        (A) NAME/KEY: Peptide
        (B) LOCATION: 1..15

(xi) SEQUENCE DESCRIPTION: SEQ ID NO: 7:

Gln Lys Arg Ala Ala Val Asp Thr Tyr Cys Arg His Asn Tyr Gly
1               5                  10                  15

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: S6

(ix) FEATURE:
        (A) NAME/KEY: Peptide
        (B) LOCATION: 1..15
```

(xi) SEQUENCE DESCRIPTION: SEQ ID NO: 8:

```
Lys Asp Leu Leu Glu Gln Lys Arg Ala Ala Val Asp Thr Tyr Cys
1               5                   10                  15
```

VACCINE COMPOSITIONS AND METHODS USEFUL IN INDUCING IMMUNE PROTECTION AGAINST ARTHRITOGENIC PEPTIDES INVOLVED IN THE PATHOGENESIS OF RHEUMATOID ARTHRITIS

RELATED U.S. PATENT APPLICATIONS

This application is a divisional of U.S. patent application Ser. No. 09/107,615, filed Jun. 30, 1998, now U.S. Pat. No. 6,153,200, which is a divisional of U.S. patent application Ser. No. 08/618,464, filed Mar. 15, 1996, now U.S. Pat. No. 5,773,570, which is a continuation in part of U.S. patent application Ser. No. 08/246,988, filed May 20, 1994, now abandoned, all of which are hereby incorporated by reference in their entirety.

STATEMENT OF FEDERALLY SPONSORED RESEARCH

This invention was made with Government support under Grant No. AR25443 by the National Institute of Health. The Government may have certain rights in this invention.

BACKGROUND OF THE INVENTION

1. Field of the Invention

The invention relates to the control and prevention of autoimmune disease, in particular rheumatoid arthritis. More specifically, the invention relates to methods and reagents which reduce or prevent the response of a host to arthritogenic peptides which include an amino acid sequence (Q(K/R)RAA) that is homologous to a sequence contained in certain HLA proteins.

2. History of the Prior Art

In humans, autoimmune diseases such as rheumatoid arthritis tend to be associated with particular HLA specificities. Rheumatoid arthritis (RA) in particular is presently believed to be associated on a genetic level with the Class II HLA haplotypes DW4, DW14, DW15 (all with DR4 specificity) and/or DR1. Each of these haplotypes include an amino acid sequence which is commonly referred to as the "susceptibility sequence" (hereafter, "RA susceptibility sequence"; see SEQ ID NOs: 1 and 2). The RA susceptibility sequence is known to vary at one amino acid; to wit, QRRAA (SEQ ID NO: 3) and QKRAA (SEQ ID NO: 2) (hereafter, "Q(R/K)RAA"). More than 90% of adult patients with seropositive RA have also been found to have HLA DR antigens with the RA susceptibility sequence in the third hypervariable region of the molecule. The RA susceptibility sequence has not been implicated in the onset of juvenile RA (JRA), except in patients suffering from severe, seropositive JRA.

The QRRAA (SEQ ID NO: 3) variant of the susceptibility sequence has been identified on HLA haplotypes DW14, DW15 and DR1. The QKRRA (SEQ ID NO: 2) variant has been identified on HLA haplotype DW4. Highly conserved homologs of the variants have also been identified in the Epstein-Barr virus glycoprotein gp110, as well as the dnaJ heat shock proteins from *Escherichia coli*, as well as the bacterial species *Klebsiella, Ptoteus, Salmonella*, and *Lactococcus*.

In 1992, Albani, et al., *J. Clin. Invest.*, 89:327–331 (1992) published a report indicating that they had expressed and purified recombinant dnaJ (rdnaJ). The purified rdnaJ was specifically bound by antisera raised in rabbits against the RA susceptibility sequence from DW4 proteins. Antisera raised against rdnaJ also bound the intact DW4 protein in vitro as well as DW4 homozygous B lymphoblasts. No role or mechanism for in vivo activity on the part of rdnaJ in rheumatoid arthritis was proposed.

One approach to utilize the RA susceptibility sequence to treat RA has been proposed which would vaccinate humans against RA with certain RA susceptibility sequence peptides derived from known human HLA peptides (see, published PCT application, WO 9014835 (filed May 31, 1990), Carson, et al., inventors).

Another therapeutic modality for controlling the immune response to bacterial antigens has been proposed in U.S. Pat. No. 4,732,757 to Stolle, et al. Stolle, et al. proposed administering IgG antibodies raised in cow's milk against a broad spectrum of intact bacteria which typically reside in the human gastrointestinal tract. The IgG tested by Stolle, et al., were raised against a mixture of intact organisms without targeting specific bacterial antigens. This patent issued prior to the identification of the RA susceptibility sequence in certain bacterial heat shock proteins, including dnaJ. The antisera described by Stolle, et al. were not, therefore, directed toward RA susceptibility sequence peptides.

None of these approaches to treating RA specifically target arthritogenic peptides before the peptides are presented to the systemic immune system of an RA patient. A need, therefore, exists for a treatment which will not only ameliorate systemic responses by an RA patient to arthritogenic peptides, but will also prevent pathogenic exposure of the patient to the arthritogenic peptides through the release of such peptides from the patient's GI tract into systemic circulation. Ideally, such treatments will be provided either before the patient develops RA or in the early stages of the disease; thus, a need also exists for a method of identifying persons who are genetically and immunologically predisposed to develop RA.

The present invention addresses each of these needs.

SUMMARY OF THE INVENTION

The invention comprises methods for reducing or avoiding host sensitization to arthritogenic peptides, particularly dnaJ. For purposes of this disclosure, the phrase "arthritogenic peptides" will, unless context otherwise requires, refer to proteins and peptide fragments thereof which contain the RA susceptibility sequence.

Surprisingly, one dnaJ peptide in particular (hereafter, "dnaJp1"; SEQ.ID.No.4) has been found to induce relatively strong immune responses in seropositive adult RA patients. In one aspect of the invention, the relatively great antigenicity of dnaJp1 is used to advantage in dnaJp1 peptide vaccines. Such vaccines utilize dnaJp1 of microbial, synthetic or recombinant sources, and preferably comprise mixtures of antigenic dnaJp1 with dnaJ peptides or human dnaJ peptide homologs. Alternatively, the vaccines of the invention comprise plasmid or viral recombinant expression vectors which encode dnaJp1. Particularly preferred vaccines of the invention in inducing oral tolerance to dnaJ peptides.

In another aspect of the invention, antibodies (preferably IgA) are raised (preferably in milk) against dnaJp1 and administered (preferably by enteral routes and preferably as Fab fragments of the Ig) to an RA patient.

The invention also comprises a method for screening candidates for the above-described therapies by (1) measuring cellular and humoral immune responses to an arthritogenic peptide, and (2) detecting the RA susceptibility sequence in the individual's HLA DR antigens.

The details of the preferred embodiment of the present invention are set forth in the accompanying drawings and the description below. Once the details of the invention are known, numerous additional innovations and changes will become obvious to one skilled in the art.

$$\% \text{ inhibition} = 100 \frac{1 - OD_{460} \text{with } rdnaJ}{(OD_{460} \text{without } rdnaJ)}$$

The control sera were obtained from humans without RA.

Figure 4:
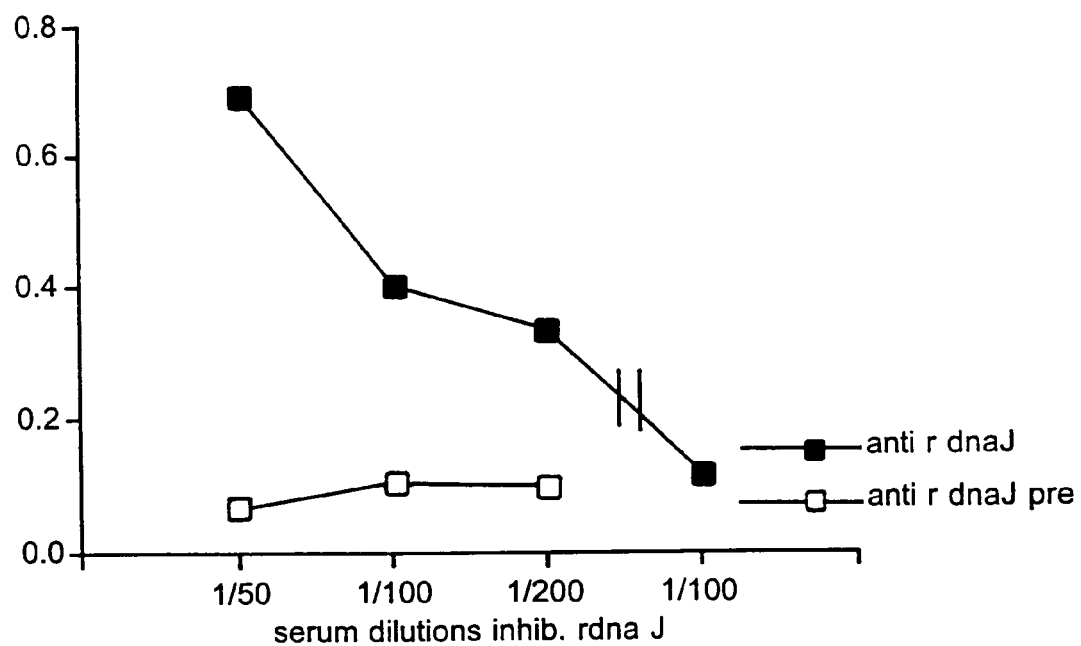

FIG. 4 depicts the in vitro antibody response of rabbit sera to rdnaJ as measured by an enzyme-linked immunosorbent assay. The results are expressed as the mean OD at 405 nm of duplicate plate wells.

FIG. 5 is a table comparing the binding efficiencies of several dnaJ peptides for purified HLA MHC Class II epitopes. Binding was detected by ELISA between biotinylated dnaJ peptides and immobilized HLA molecules. The results are expressed in the table as absorption units at 405 nm. The peptides tested were: dnaJp1 (SEQ.ID.No.4), dnaJpV (SEQ.ID.No.5), dnaJp2 (SEQ.ID.No.6), S1 (SEQ.ID.No.7) and S6 (SEQ.ID.No.8). S1 and S2 are synthetic peptides whose amino acid sequence corresponds to the sequence of known HLA DR antigens.

DETAILED DESCRIPTION OF THE INVENTION

I. Activity of the Vaccines of the Invention

Human patients with early stage RA have been discovered to have abnormally high cellular immune responses to a microbial peptide having the RA susceptibility sequence. This observation leads to the conclusion that RA is triggered or exacerbated by immune responses to sterile fragments of bacterial antigens that are transported to the joints by monocytes. Further, the molecules involved in these immune responses are likely to be cross-reactive with the RA susceptibility sequence on HLA DW4 and DR1.

Although the invention is not limited to or dependent upon any particular theory concerning the pathogenesis of RA, the following discussion is provided as an explanation of why and how the methods of the invention exploit the immune mechanism likely to be involved in RA.

The granulation tissue of the rheumatoid pannus is filled with cells of the monocytic lineage. In humans (as opposed to lower animals) these tissue macrophages do not divide efficiently, and must be replenished continually from circulating blood monocytes. It is reasonable to suppose that immune complexes containing dnaJ or dnaJ peptide fragments (such as dnaJp1) and IgG antibodies thereto form first in the intestinal mucosal region, and are picked up by circulating blood monocytes with Fc receptors.

Some of these antigen-loaded monocytes will migrate systemically to the joints. The T lymphocytes from individuals with the RA susceptibility sequence have probably been educated to hyper-respond to certain arthritogenic peptides, such that tiny amounts of antigen would suffice to initiate joint inflammation. Such very small quantities of a common bacterial antigen might never be detected by classic immunologic means.

Once established, synovitis could be sustained by the further development of antibodies to the immune complexed IgG (rheumatoid factors), and to degraded components of cartilage and connective tissue. However, at least the early stages of rheumatoid arthritis may depend upon the continual loading of circulating monocytes with IgG immune complexes containing arthritogenic peptides.

Figure 2:
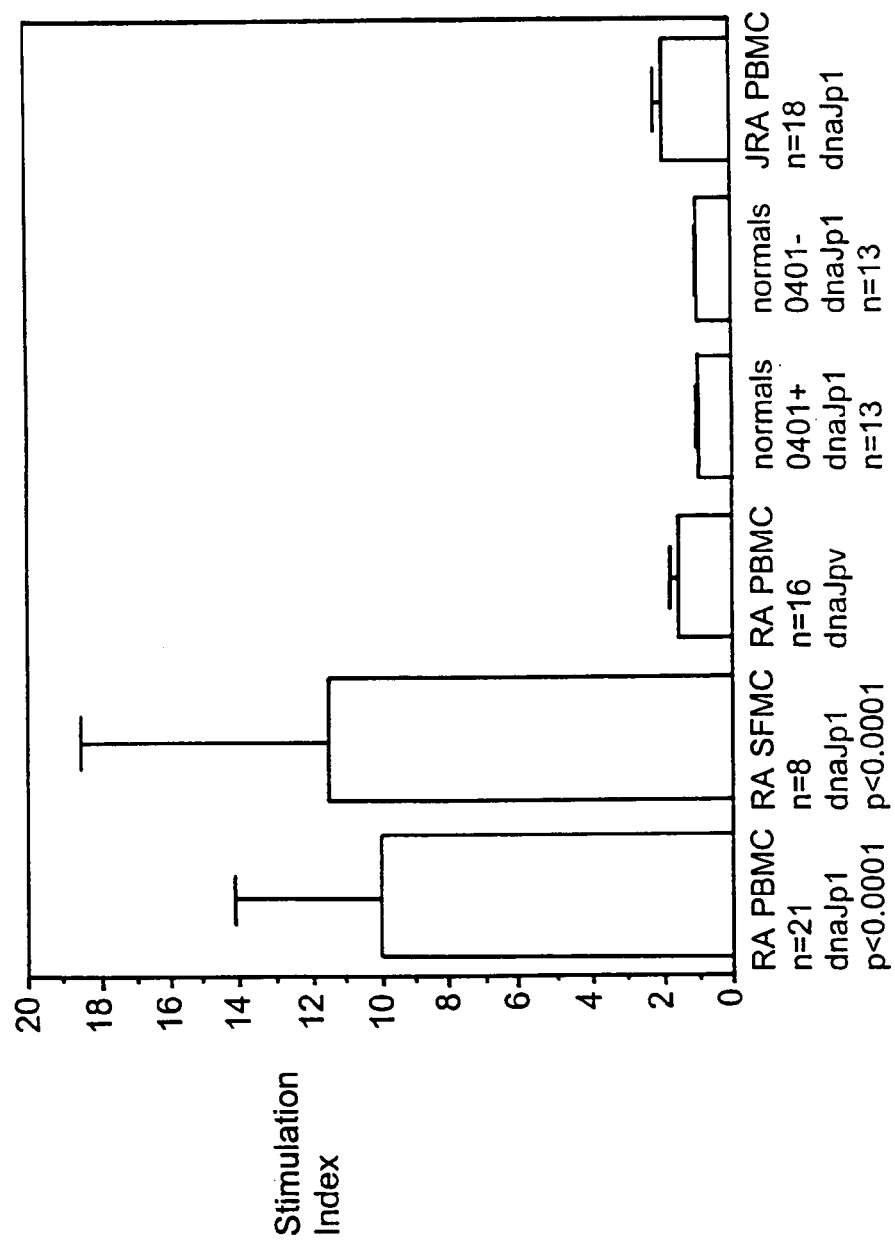
FIG. 2 quantifies proliferation of cultured lymphocytes from adult RA and juvenile RA (JRA) patients following exposure of the cells to synthetic dnaJp1 (amino acid sequence QKRAAYDQYGHAAFE; SEQ.ID.No.4) or a mutant dnaJ peptide having the amino acid sequence DERAAYDQYGHAAFE ("dnaJpV"; SEQ.ID.No.5). The control culture tested consisted of lymphocytes obtained from adults without RA ("normals"). The responses shown by bars in the graph of FIG. 2 are expressed in terms of a lymphocyte stimulation index; i.e., (CPM detected in cultures with dnaJ)/(CPM detected in cultures without dnaJ).

The immune response to one particular dnaJ peptide has proven to be a surprisingly strong one. As shown in FIG. 2, dnaJp1 peptide (SEQ.ID.No.4) stimulates proliferation by lymphocytes from the blood of adult RA patients at a magnitude of nearly 10 times the response of the same cells to dnaJpV peptide (SEQ.ID.No.5), which differs in sequence from dnaJp1 by only two amino acids. The dnaJp1 peptide binds HLA MHC Class II molecule epitopes more strongly—by a magnitude of 100 times or more—than do human HLA Dw4 peptides (e.g., S1 and S6; SEQ.ID.Nos. 7–8) which also contain the RA susceptibility sequence. These differences in binding affinity would acount for the strong T cell responses seen in early rheumatoid arthritis patients.

Methods for identifying suitable candidates for treatment with the inventive vaccines are disclosed below.

II. Vaccine Compositions of the Invention

The invention utilizes dnaJp1 as an antigen in a vaccine to provide protection against in vivo responses to arthritogenic peptides. In particular, according to the invention, an adult diagnosed as having or being at risk for the onset of RA, and juveniles diagnosed as having or being at risk for the onset of seropositive RA, will be treated with a therapeutically effective dosage of a dnaJp1 vaccine composition. dnaJp1 vaccines of the invention comprise (1) vaccine compositions comprised of purified dnaJp1 peptide, synthetic dnaJp1 peptide or recombinant dnaJp1 peptide; (2) vaccine compositions comprised of dnaJp1 peptide and one or more human dnaJ homologs; (3) vaccine compositions comprised of dnaJp1 peptide and one or more other peptide fragments of dnaJ protein; or (4) vaccine compositions of plasmid or viral recombinant expression vectors which encode dnaJp1 peptide.

A. Peptide Vaccine Compositions

Techniques for purifying, synthesizing or producing peptides in recombinant form are well-known in the art and are suitable for production of antigenic peptides of sufficient purity for use in the invention. In this respect, the term "substantially pure" denotes a protein which is substantially free of other compounds with which it may normally be associated in vivo. In the context of the invention, the term refers to homogenous proteins or peptides containing the RA susceptibility sequence (in particular dnaJp1, dnaJ peptides and human dnaJ peptide homologs), where homogenicity is determined by reference to purity standards known to those of ordinary skill in the art (such as purity sufficient to allow the N-terminal amino acid sequence of the protein to be obtained).

Substantially pure arthritogenic proteins and peptides may be obtained from intact microorganisms (particularly bacteria), through microbial expression, by synthesis, and/or by purification means known to those skilled in the art, such as affinity chromatography. Such techniques may be utilized to obtain antigenic peptide fragments of dnaJ, including dnaJp1.

Amino acid sequences for dnaJp1 and several other dnaJ protein fragments (peptides) are set forth in the Sequence Listing appended hereto as SEQ. ID. Nos. 4–6. Further, the full-length amino acid sequence for the *E. coli* dnaJ protein is set forth in SEQ ID NO: 1. The intact protein and each peptide described are antigenic, although the antigenic activity of the dnaJp1 peptide is substantially greater than the activity of the other dnaJ peptides described.

The nucleotide and amino acid sequences of several other bacterial dnaJ proteins and human dnaJ homologs are known. For example, the amino acid sequence for *Lactococcus lactis* dnaJ is reported in Van Asseldonk, et al., *J. Bact.*, 175:1637–1644 (1993). Further, dnaJ human homolog amino acid and/or nucleotide coding sequences (lacking the RA susceptibility sequence) have been reported by Chellaiah, et al., *Biochem. Biophys. Acta,* 117:111–113, 1993; Oh, et al., *Biochem. Biophys. Acta,* 117:114–116, 1993; Raabe and Manley, *Nuc. Acids Res.,* 19:6645, 1992; and, Sugito, et al., *FEBS Lett.,* 358:161–164, 1995. The disclosures of these references are hereby incorporated into this disclosure for reference in identifying and constructing vaccine components for mixture with dnaJp1 peptide or dnaJp1 coding polynucleotide according to the invention.

With reference to such sequences, proteins and peptides useful in the vaccine compositions of the invention can be synthesized by such commonly used methods as t-BOC or FMOC protection of alpha-amino groups. Both methods involve stepwise syntheses whereby a single amino acid is added at each step starting from the C terminus of the peptide (see, Coligan, et al., *Current Protocols in Immunology,* Wiley Interscience, 1991, Unit 9). Peptides of the invention can also be synthesized by various well known solid phase peptide synthesis methods, such as those described by Merrifield (*J. Am. Chem. Soc.,* 85:2149, 1962), and Stewart and Young (*Solid Phase Peptides Synthesis,* Freeman, San Francisco, 1969, pp 27–62), using a copoly (styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C.

After evaporation of the reagents, the peptides are extracted from the polymer with 1% acetic acid solution which is then lyophilized to yield the crude material. This can normally be purified by such techniques as gel filtration on a "SEPHADEX® G-15" or "SEPHAROSE®" affinity column using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and sequenced by the solid phase Edman degradation.

Depending on the patient's presenting condition, it may also be desirable to administer immunostimulants and/or immunosuppressants whose action will be directed to the patient's systemic immune system. Suitable substances having this activity are well-known in the art and include interleukin-6 (for stimulation of suppressor/cytotoxic T cells) as well as cyclosporin A and anti-CD4 antibodies (for immune suppression). Such compounds may be administered separately or as a mixture with a vaccine of the invention.

The dnaJp1 peptide vaccines of the invention may be prepared for administration by mixing the active components of the vaccine with physiologically acceptable carriers. Such carriers will be nontoxic to recipients at the dosages and concentrations employed. Ordinarily, the preparation of such compositions entails combining the particular vaccine antigen with saline, buffers, antioxidants such as ascorbic acid, low molecular weight (less than about 10 residues) polypeptides, proteins, amino acids, carbohydrates including glucose or dextrins, or chelating agents such as EDTA, glutathione and other stabilizers and excipients. Such compositions may be in suspension, emulsion or lyophilized form and will be pharmaceutically acceptable; i.e., suitably prepared and approved for use in the desired application.

With respect to compositions containing TGF-β, compounds of the TGF-β family are ordinarily produced in the form of inert precursors that are activated by exposure to acid or proteases. Those of ordinary skill in the art will, therefore, be able to select carriers and/or excipients for use in the RA vaccine compositions of the invention which will neither interfere with the in vivo activation of the TGF-β component or activate the component prematurely (i.e., prior to administration of the composition).

B. Nucleotide Vaccines of the Invention

Certain advantages may be obtained by administering dnaJp1 coding polynucleotides as a "gene vaccine" in lieu of administering the peptide as a traditional antigen vaccine. For example, the risk of potential toxicity (e.g., anaphylatic shock) associated with proteinaceous antigen vaccines is substantially avoided if a polynucleotide encoding the antigen is administered and expressed in vivo in lieu of the antigen itself.

As used herein, "polynucleotide" refers to a polymer of deoxyribonucleotides or ribonucleotides, in the form of a separate fragment or as a component of a larger construct. The dnaJ/dnaJp1 peptide coding polynucleotides of the invention may be double or single-stranded DNA or RNA inserted into recombinant gene expression vectors. Such polynucleotides should also be either non-replicating or engineered by means well known in the art so as not to replicate into the host genome.

Coding nucleotide sequences for dnaJp1 and other antigenic, immunostimulatory or immunosuppressive peptides of interest in the invention may be readily determined (if not known) by deduction from the amino acid sequence of the peptide, taking into account the degeneracy of the bacterial and human genomes. The coding polynucleotide sequence for dnaJ protein (including dnaJp1) is provided in the appended Sequence Listing as SEQ.ID.No.1.

Screening procedures which rely on nucleic acid hybridization make it possible to isolate any polynucleotide sequence from any organism, provided the appropriate probe or antibody is available. Oligonucleotide probes, which correspond to a part of the sequence encoding the protein in question, can be synthesized chemically. This requires that short, oligo-peptide stretches of amino acid sequence must be known or deduced.

For example, a cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of peptides of interest having at least one epitope using antibodies specific for the peptides. Such antibodies can be either polyclonally or monoclonally derived and used to detect expression product indicative of the presence of cDNA of interest.

Polynucleotides for use in the invention can also be synthesized using techniques and nucleic acid synthesis equipment which are well-known in the art. For reference in this regard, see Ausubel, et al., *Current Protocols in Molecular Biology*, Chs. 2 and 4 (Wiley Interscience, 1989) (genomic DNA); and, Maniatis, et al., *Molecular Cloning: A Laboratory Manual* (Cold Spring Harbor Lab., New York, 1982) (cDNA). For ease of construction and use, synthesized polynucleotides and cDNAs are generally preferred for use in the recombinant gene expression vectors of the invention.

The recombinant gene expression vectors of the invention are preferably plasmids or cosmids which include the antigen coding polynucleotides of the invention, but may also be viruses or retroviruses. Preferably, the vectors are "naked"; i.e., not associated with a delivery vehicle (e.g., liposomes, colloidal particles and the like). For convenience, the term "plasmid" as used in this disclosure will refer to plasmids or cosmids, depending on which is appropriate to use for expression of the peptide of interest (where the choice between the two is dictated by the size of the gene encoding the peptide of interest). "Operatively encode" refers to a gene which is associated with all of the regulatory sequences (e.g., promoters) required for expression of a polypeptide.

A commonly used plasmid vector which operatively encodes foreign structural gene inserts is the pBR322 PLASMID. pBR322 includes a gene for conferring ampicillin resistance as a marker; however, for use in humans, such ampicillin resistance should be avoided. Modified vectors which are useful in gene immunization protocols but do not confer ampicillin resistance are described in commonly owned U.S. patent application Ser. No. 08/593,554, filed Jan. 30, 1996, the disclosure of which is incorporated herein by this reference.

Various viral vectors that can be utilized in the invention include adenovirus, herpes virus, vaccinia, or an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuS-V), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, Ψ2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

For administration, nucleotide vaccines of the invention may be composed in a carrier such as saline or, less desirably, may be administered with a delivery vehicle, such as a liposome or colloidal particles. Methods for preparation and use of such delivery vehicles will be well-known to, or may be readily ascertained by, those of ordinary skill in the art.

II. Reagents and Methods for Use in Identifying Suitable Candidates for the Therapeutic Methods of the Invention A. Characteristics of Suitable Candidates for the Therapeutic Methods of the Invention.

The principal candidates for the therapeutic methods of the invention are individuals who have early stage RA or who are predisposed to develop the disease. In this regard, with one caveat, an individual may be considered to be "predisposed" to develop RA when their HLA molecules contain the RA susceptibility sequence.

The caveat, however, is based on the observation that certain "normal" individuals (i.e., who do not have a family history of RA and do not develop it themselves) may nonetheless have endogenous HLA DR antigens which bear the RA susceptibility sequence. Yet despite the presence of the RA susceptibility sequence in these individuals, they may never develop an autoimmune response to RA susceptibility sequence HLA antigens.

Figure 3:
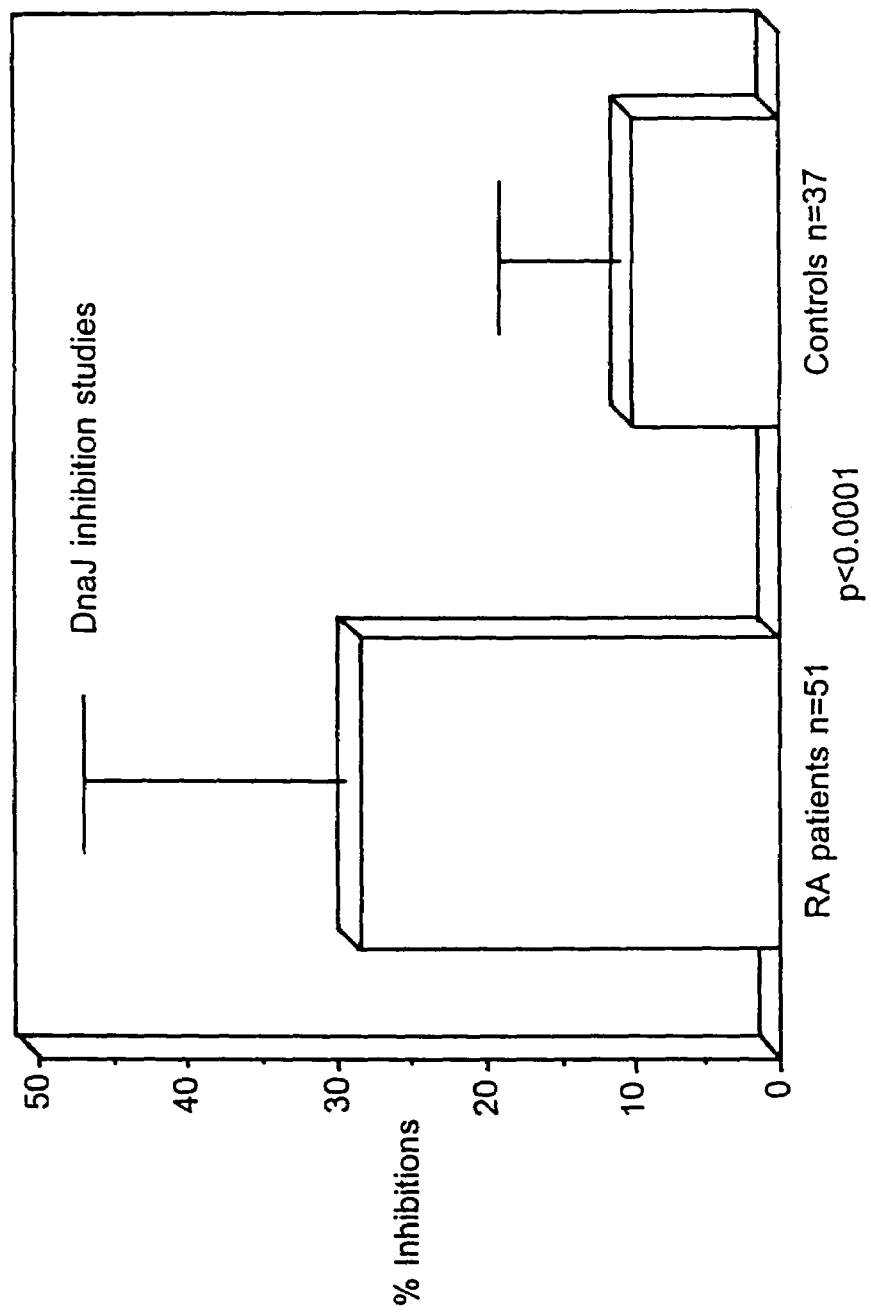
FIG. 3 depicts the results of an inhibition study for inhibition of the activity of anti-dnaJ antibodies produced in separate sera samples from 51 early stage RA patients by intact dnaJ. The percent inhibition shown by bars in the graph of FIG. 3 is expressed in terms of the formula.

It can be presumed from the preceding observation that the development of RA is most likely associated not only with the education of the T cell repertoire to recognize the RA susceptibility sequence as non-self, but also to the production in RA sufferers of anti-RA susceptibility sequence antibodies (see, Example IV and FIG. 3, showing inhibition of antibody binding in lymphocytes from RA patients by dnaJ, where the magnitude of the inhibition substantially exceeds that observed in lymphocytes from normal individuals). Thus, individuals whose HLA antigens bear the RA susceptibility sequence and who produce anti-RA susceptibility sequence antibodies will, for purposes of this disclosure, be considered to be "predisposed" to RA. A screening method for identification of individuals with early stage RA or who are predisposed to it (the "RA screening method") is described below.

B. Steps of the RA Screening Method.

The RA screening method will generally comprise the steps of (1) detecting whether the RA susceptibility sequence is present on HLA molecules from an individual (in particular, DW4 molecules), and (2) detecting whether lymphocytes from the individual produce antibodies in response to being exposed to an antigenic form of an arthritogenic protein or peptide (particularly dnaJp1). Alternatively, the screening method may entail only the latter step because if the individual's lymphocytes produce antibodies in response to being exposed to an RA susceptibility sequence protein, the individual may be presumed to be more likely to develop RA.

To perform the HLA typing step of the RA screening method, a biological sample, which may be any fluid or tissue likely to contain lymphocytes, but will preferably be whole peripheral blood or synovial fluid (the "lymphocyte sample"), will be obtained using conventional techniques from the individual to be screened for RA. To determine whether the individual's HLA molecules bear the RA susceptibility sequence, conventional HLA typing techniques well-known to those skilled in the art may be employed. It will be appreciated in this regard that the nucleotide and amino acid sequences for most known HLA antigens have been fairly well characterized and can be readily identified (see, e.g., Marsh, et al., Tissue Antigens, 37:181–189 (1991), and Bodmer, et al., Tissue Antigens, 37:97–105 (1991)).

For example, with reference to the polynucleotide sequences reported by Marsh and Bodmer, et al., and/or the polynucleotide sequences contained in the Sequence Listing appended hereto, those of ordinary skill in the art will be able to construct oligonucleotide probes which will hybridize to target polynucleotide sequences for detection of specific HLA antigens in a lymphocyte sample. Techniques for construction of suitable probes and performance of hybridization techniques are described in greater detail infra and may be employed by those of ordinary skill in the art without undue experimentation.

Commonly, however, HLA typing is performed serologically, i.e., by using standardized antisera (of defined specificity) to a lymphocyte sample together with complement and observing whether the test cells are killed. HLA typing may also be performed by other conventional immunological techniques such as the "Mixed Lymphocyte Reaction" wherein test lymphocytes are mixed with B lymphocytes of defined HLA specificity. In the Mixed Lymphocyte Reaction, test cells of specificity different than the B cells of known HLA type are stimulated and proliferate. Performance of all of these HLA typing techniques is well within the ordinary level of skill in the art.

To perform the immunoassay step of the RA screening method, the arthritogenic peptides may be detected in a lymphocyte sample using anti-arthritogenic peptide antibodies in either liquid or solid phase immunoassay formats (when bound to a carrier). Antibodies for use in these formats may be produced as described infra.

Examples of well-known carriers for use in solid-phase assay formats include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

Examples of types of immunoassays which can utilize anti-arthritogenic antibodies of the invention are competitive and non-competitive immunoassays in either a direct or indirect format. Examples of such immunoassays are the ELISA, the radioimmunoassay (RIA), and the sandwich (immunometric) assay. Binding of arthritogenic peptides using the antibodies of the invention can be done utilizing immunoassays which are run in either the forward, reverse, or simultaneous modes, including immunohistochemical assays on physiological samples. Those of skill in the art will know, or can readily discern other immunoassay formats without undue experimentation.

The protocol described in Example V illustrates how the RA screening method may be performed by immunoassay (there, an enzyme-linked immunoadsorbent assay, or ELISA). In a preferred embodiment of the RA screening method, lymphocytes obtained by conventional means from persons who are suspected of having early stage RA or of being predisposed to the disease are cultured and exposed to antigenic RA susceptibility peptides, preferably dnaJp1 (SEQ.ID.No.4, produced as described supra). The cellular immune response of the cultured lymphocytes to the antigenic dnaJ peptide is then detected. Alternatively, the protocol may be performed as an inhibition study as described in Example IV; i.e., where any reduction in antibody binding through preincubation with dnaJp1 peptide is detected.

The anti-arthritogenic peptide antibodies of the invention may also be detectably labelled. There are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the anti-arthritogenic peptide antibodies of the invention, or will be able to ascertain such, using routine experimentation. Furthermore, the binding of these labels to the anti-arthritogenic peptide antibodies of the invention can be done using standard techniques common to those of ordinary skill in the art. Another labeling technique which may result in greater sensitivity consists of coupling the antibodies to low molecular weight haptens. These haptens can then be specifically detected by means of a second reaction. For example, it is common to use haptens for this purpose such as biotin, which reacts with avidin.

To differentiate between an individual whose HLA DR antigens molecules bear the RA susceptibility sequence peptide but who is nonetheless not predisposed to RA from one who is genetically disposed to RA, the ability of the individual to produce an immune response to antigenic dnaJ or RA susceptibility sequence peptide may also be tested. To that end, a lymphocyte sample is incubated with an antigenic arthritogenic peptide. Any anti-arthritogenic peptide antibodies produced in the sample are then detected by an appropriate immunoassay format as described above or in Example V. For convenience of detection, the antigenic arthritogenic protein or peptide may be detectably labelled as described above.

C. Reagents and Kits for Use in the Screening Methods.

Reagents for use in the RA screening method of the invention include arthritogenic peptides (preferably those produced synthetically or by recombinant means as described above), antibodies for immunoassays, and oligonucleotide probes and primers which complement and specifically hybridize to HLA molecule encoding polynucleotides for use in hybridization assays for HLA screening. Kits containing one or more of these reagents in a convenient, storable package for use in performing the RA screening method are included within the scope of the invention.

Methods to obtain peptides and oligonucleotides which will be of use in the screeing method of the invention are described elsewhere above. Antibodies for use in this method of the invention may be raised against intact arthritogenic proteins, as well as synthetic or recombinant peptides. Such peptides will include the RA susceptibility sequence and preferably consist of dnaJp1 (SEQ.ID.No.4).

For example, suitable antigenic, arthritogenic peptides for use in the method of the invention are described in the Sequence Listing appended hereto as SEQ ID NOs: 4 and 5. The amino acids following the RA susceptibility sequence in SEQ ID NOs: 4 and 5 are likely not required for T-cell activation by the RA susceptibility sequence, but do cause the peptide to be highly charged and, therefore, antigenic. To that end, preferred antigenic, arthritogenic peptides for use in producing the antibodies of the invention will be at least about 7–15 amino acids in total length.

Preferably, the antibodies will be raised against recombinant arthritogenic peptides to ensure that the antisera are specific for the RA susceptibility sequence and to enable production of antigenic peptides on a relatively large scale. Most preferably, the antibodies of the invention will be raised in milk, such as bovine milk, to selectively stimulate production of IgG (thus enhancing the specificity of the antisera for arthritogenic peptides rather than other GI bacterial antigens).

The antibodies of the invention will also be useful to detect the presence of the RA susceptibility sequence on HLA molecules, in populations of E. coli. from the GI tract of an individual, and in certain therapeutic modalities described infra.

To induce an immune response to dnaJ or another arthritogenic protein or peptide in a normal animal, the antigenicity of the protein or peptide may be enhanced by coupling to a carrier protein by conjugation using techniques which are well-known in the art. Such commonly used materials which are chemically coupled to the molecule to enhance their antigenicity include keyhole limpet hemocyanin (KLH), thyroglobulin, bovine serum albumin (BSA), and tetanus toxoid. The coupled molecule is then used to immunize the animal (e.g., a mouse, rabbit or cow).

A multiple injection immunization protocol is preferred for use in immunizing animals with antigenic protein (see, e.g., Langone, et al., eds., "Production of Antisera with Small Doses of Immunogen: Multiple Intradermal Injections", *Methods of Enzymology*, Acad. Press, 1981). For example, an antibody response can be obtained in rabbits by intradermal injection of 1 mg of antigenic protein emulsified in Complete Freund's Adjuvant followed several weeks later by one or more boosts of the same antigen in incomplete Freund's Adjuvant. A particularly preferred method for production of therapeutic antibodies of the invention in cows is described further infra.

Polyclonal antibodies produced by the immunized animals can be further purified, for example, by binding to and elution from a matrix on which the protein or peptide to which the antibodies were raised is bound. Those of skill in the art will know of various techniques common in the immunology arts for purification and/or concentration of polyclonal antibodies, as well as monoclonal antibodies (see, for example, Coligan, et al., *Current Protocols in Immunology*, Unit 9, (Wiley Interscience, 1991)).

For preparation of monoclonal antibodies, immunization of a mouse or rat is preferred. The term "antibody" as used in this invention is meant also to include intact molecules as well as fragments thereof, such as for example, Fab and F(ab')$_2$, which are capable of binding an arthritogenic protein or peptide. Also, in this context, the term "mAb's of the invention" refers to monoclonal antibodies with specificity for an arthritogenic protein or peptide.

The general method used for production of hybridomas secreting monoclonal antibodies ("mAb's") is well known (Kohler and Milstein, *Nature*, 256:495, 1975). Briefly, as described by Kohler and Milstein, the technique comprised isolation of lymphocytes from regional draining lymph nodes of five separate cancer patients with either melanoma, teratocarcinoma or cancer of the cervix, glioma or lung. The lymphocytes were obtained from surgical specimens, pooled, and then fused with SHFP-1. Hybridomas were screened for production of antibody which bound to cancer cell lines. An equivalent technique can be used to produce and identify mAb's with specificity for an arthritogenic protein.

Confirmation of arthritogenic protein specificity among mAbs of the invention can be accomplished using relatively routine screening techniques (such as the enzyme-linked immunosorbent assay, or "ELISA") to determine the elementary reaction pattern of the mAb of interest.

It is also possible to evaluate an mAb to determine whether is has the same specificity as mAb of the invention without undue experimentation by determining whether the mAb being tested prevents a mAb of the invention from binding to an RA arthritogenic protein. If the mAb being tested competes with the mAb of the invention, as shown by a decrease in binding by the mAb of the invention, then it is likely that the two monoclonal antibodies bind to the same or a closely related epitope.

Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it binds the same epitope as a mAb of the invention.

III. Therapeutic Methods of the Invention

A. Methods for Use of the Vaccines of the Invention

The peptide vaccines of the invention are preferably administered in a manner sufficient to selectively stimulate IgA production in the patient's GI tract and induce oral tolerance (see, regarding oral tolerance induction through antigen feeding in animals and humans generally, Husby, et al., *J. Immunol.* 152:4663–4670 (1994), the disclosure of which is incorporate herein by this reference to illustrate the state of knowledge in the art concerning oral tolerance to antigens). Therefore, the antigenic peptides of the invention will preferably be administered concomitantly with an immunostimulant which is known in the art to induce IgM switching to IgA; e.g., TGF-β, which may also inhibit systemic helper T cell activity. Most preferably, the antigenic peptide/IgA immunostimulant of the invention will be administered enternally to localize the effect of the vaccine in the GI tract. Alternatively, the peptide vaccines of the invention may be administered in any manner accepted in the immunotherapeutic art; e.g., intravascularly.

The preferred method for administration of the nucleotide vaccines of the invention is by intradermal routes. Methods for intradermal gene immunization utilizing recombinant gene expression vectors which encode antigenic peptides of interest are disclosed in commonly owned U.S. patent application Ser. No. 08/593,554, filed Jan. 30, 1996, and Ser. No. 08/446,691, filed Jun. 7, 1995, the disclosures of which are incorporated herein by this reference. Briefly, according to these disclosures, recombinant gene expression vectors are administered by means such as injection, absorption or transdermal transmission across the skin or mucosa of the host. Alternatively, nucleotide vaccines of the invention may be administered by any accepted means in the immunological art; e.g., intramuscular injection.

The protocol for administration of the peptide and nucleotide vaccines of the invention will vary with their composition as well as the age, weight and condition of the patient. However, a preferred protocol for administration of the RA peptide vaccines will involve daily oral (enteral) administration of immunologically effective dosages of the vaccine, with or without other forms of therapy, such as the methods described above and conventional anti-inflammatory treatments (e.g., use of steroidal or nonsteroidal anti-inflammatory medicaments and/or analgesics).

Depending on the frequency of dosage, an immunologically effective dosage of each peptide vaccine of the invention will range from 100 μg–100 mg (preferably 1–100 mg) antigenic protein or peptide. Daily dosages of antigenic peptide will most preferably be given in amounts of about 1 mg/day.

The dosage of each recombinant gene expression vector to be supplied according to the method of the invention will vary depending on the desired response by the host and the levels of gene expression achievable by the vector used. Generally, for introduction of naked recombinant gene expression vectors by intradermal routes, it is expected that up to 100–200 μg of polynucleotide can be administered in a single dosage, although as little as about 0.3 μg of polynucleotide administered through skin or mucosa can induce long lasting immune responses.

For purposes of the invention, however, it is sufficient that the naked gene expression vectors be supplied at a dosage sufficient to cause expression of the antigenic polypeptide encoded by the polynucleotide. These dosages may be modified to achieve differing immunostimulatory levels of expression. Means to confirm the presence and quantity of expressed peptides are well-known to those skilled in the art and will not, therefore, be described in detail. Certain such means are illustrated in the Examples provided below; generally, they include immunoassays (such as enzyme-linked immunosorbent assays), PCR techniques, and immunohistological analyses performed according to techniques which are well known in the art. Dosages of the administered polynucleotides can be adjusted to achieve the desired level of expression based on information provided by these detection and quantification means as well as in vivo clinical signs known to practitioners skilled in the clinical arts.

Preferably, naked gene expression vectors of the invention will be administered in in "low" doses (e.g., in mice, about 50 μg immunostimulatory polynucleotide or less). Those of ordinary skill in the art will readily be able to determine an equivalent dosage level for use in humans. Those of ordinary skill in the art will be familiar with the course of dosing employed in vaccination and immunotherapy protocols (i.e., priming, booster and maintenance dosing), which course will be suitable for use in the method of the invention.

Conventional dosages of any immunostimulant/immunosuppressant component in the RA vaccine will be used (e.g., 1–100 μg/kg interleukin-6). Such dosages will be known to, or may be readily ascertained by, those of ordinary skill in the art. Treatment in early stage RA patients may be continued through to or beyond observation of the surrogate end-point for RA described further below in Section III.B.

Vaccination of patients who are predisposed to RA, but have not developed the disease, may be accomplished by short-term administration of one or more dosages of the RA vaccines of the invention sufficient to produce detectable increases in anti-arthritogenic peptide IgA in fluids of the patient's GI tract and/or in peripheral vascular circulation. Generally, however, the preferred use of the RA vaccines of the invention will be in patients with early stage RA.

B. Indicia of Therapeutic Efficacy for the Methods of the Invention.

Generally, the efficacy of the therapeutic methods of the invention over time may be judged by an absence of clinical signs of RA in patients who are predisposed to the disease (but have not developed it). In patients who have been diagnosed as having RA, the efficacy of the methods of the invention will be measured by a lessening in the severity of a patient's symptoms or by the occurrence of a surrogate end-point for the disease.

Conventional parameters for clinical symptoms of RA and surrogate end-points for the disease are well-known to those of ordinary skill in the art, including "Ritchie Index" measurements for joint tenderness (Ritchie, et al., *Q.J. Med*, 37: 393–406 (1968)), the number of swollen joints, daily duration of morning joint stiffness, grip strength, intensity of pain on a visual analogue scale (Huskisson, *Lancet*, 2:1127–1131 (1974)), and relative levels of use of anti-inflammatory agents and/or analgesics by the patient.

Based on the results of double-blind clinical trials of an *E. coli*. extract, Brackertz, et al., *J. Rheum*. (16:19–23 (1989)) one of ordinary skill in the art would expect clinical tolerance of the RA vaccine and antibody compositions of the invention to be good. The severity of the most possible side effects (such as gastrointestinal irritation) would be expected to be low. Toxicity of these compositions may be monitored by conventional means, such as periodic laboratory evaluations through assays of such variables as hematocrit, hemoglobin, thrombocyte and rheumatoid factor levels as well as blood chemistry.

C. Passive Antibody Therapy.

As noted elsewhere above, it is believed that at least the early stages of RA depend on continual loading of circulating monocytes with IgG immune complexes containing arthritogenic proteins and peptides such as dnaJp1. This "loading" is enabled at least in part by the failure of the GI immune system to produce sufficient antibodies, particularly IgA, to prevent escape of arthritogenic protein, peptides, and/or related antigens into circulation.

Thus, another therapeutic method of the invention is therefore directed to introducing antibodies into an individual with early stage RA or who is predisposed to the disease. Preferably, such antibody therapy is practiced as an adjuvant to the vaccination protocols described above for administration of the vaccines of the invention. These antibodies may be produced as described supra and will, in that case, preferably be monoclonal antibodies and will be administered enterally, preferably in enteric coated tablet form. Alternately, the antibodies will be produced in milk as described below.

The antibodies used will be specific for dnaJ protein or dnaJp1 peptide (hereafter, "RA therapeutic antibodies"). The RA therapeutic antibodies may be raised by immunization of an animal with these antigens in native, synthetic or recombinant form. The antigens used may be derived from any organism which expresses the RA susceptibility sequence (in particular, as part of dnaJp1), but will preferably be raised against microorganisms which reside in the gut and express the peptide as part of a heat shock protein. Most preferably, the antigens will be derived from *E. coli*. (due to the prevalence of this species in the human GI tract), but may also be raised against a cocktail of antigens from different microbial species to ensure that the antibodies will be specific for arthritogenic proteins and peptides from a broad spectrum of organisms.

To develop RA therapeutic antibodies in milk (which may then be administered therapeutically as "immune milk"), lactating mammals, preferably cows, are immunized with antigenic RA susceptibility sequence peptide as generally described supra. Cow's milk is the preferred medium for production of RA therapeutic antibodies due to its absorbability into the human GI tract. The milk may be collected, pasteurized and, preferably, lyophilized for storage by conventional techniques and used as a dry milk powder. The immune milk powder may be administered in powder or reconstituted form by enteral routes generally as described in U.S. Pat. No. 4,732,737, the disclosure of which (from column 8, line 5 through column 14, line 11) is incorporated herein by reference.

The invention having been fully described, its practice is illustrated by the examples provided below. However, such examples should not be construed as limiting the scope of the invention, which is defined by the appended claims.

EXAMPLE I

Cloning, Expression and Purification of E. Coli

A 1.1-kb DNA fragment containing the E. coli dnaJ gene (see, SEQ ID NO: 1) was amplified by polymerase chain reaction from a recombinant phage encompassing the dnaK and dnaJ genes of E. coli. The polymerase chain reaction product was subcloned in the Xba 1 site of the vector PCG808fX (New England Biolabs, Beverly, Mass.) and expressed as a maltose binding fusion protein that was purified by filtration on any amylose column and elution in an amylose buffer. A rabbit antiserum to the fusion protein was used to purify rdnaJ expressed by cloning in the Xba 1 site of a pUC 19 vector. To this end, rabbit IgG were purified on immobilized protein A (Pierce Chemical Co., Rockford, Ill.) and coupled to an agarose support matrix (AFFI-GEL Hz, a trademarked product of Bio-Rad Laboratories, Richmond, Calif.). $^r$dnaJ was then obtained by running the raw cellular extracts through the affinity column and eluting the bound protein in glycine buffer, pH 2.5. Polyacrylamide gel electrophoresis of the purified product showed one unique band with the expected molecular mass of 41 kD.

EXAMPLE II

Response of Lymphocytes from Patients with Early Stage RA to rdnaJ

Lymphocytes from patients with early untreated rheumatoid arthritis (RA) were obtained from blood (peripheral blood lymphocytes, or "PBL's") for from synovial fluids using standard aseptic techniques. The cells were incubated for 7 days with purified recombinant E. coli dnaJ (10 μg/ml, obtained as described in Example I) in RPMI 1640 medium supplemented with 10% prescreened human AB type serum. Lymphocytes from 10 control subjects (i.e., persons without RA) were treated similarly. Proliferation during the last 16 hours of culture was expressed as a stimulation index=cpm in cultures with dnaJ/cpm in cultures without dnaJ.

Figure 1:
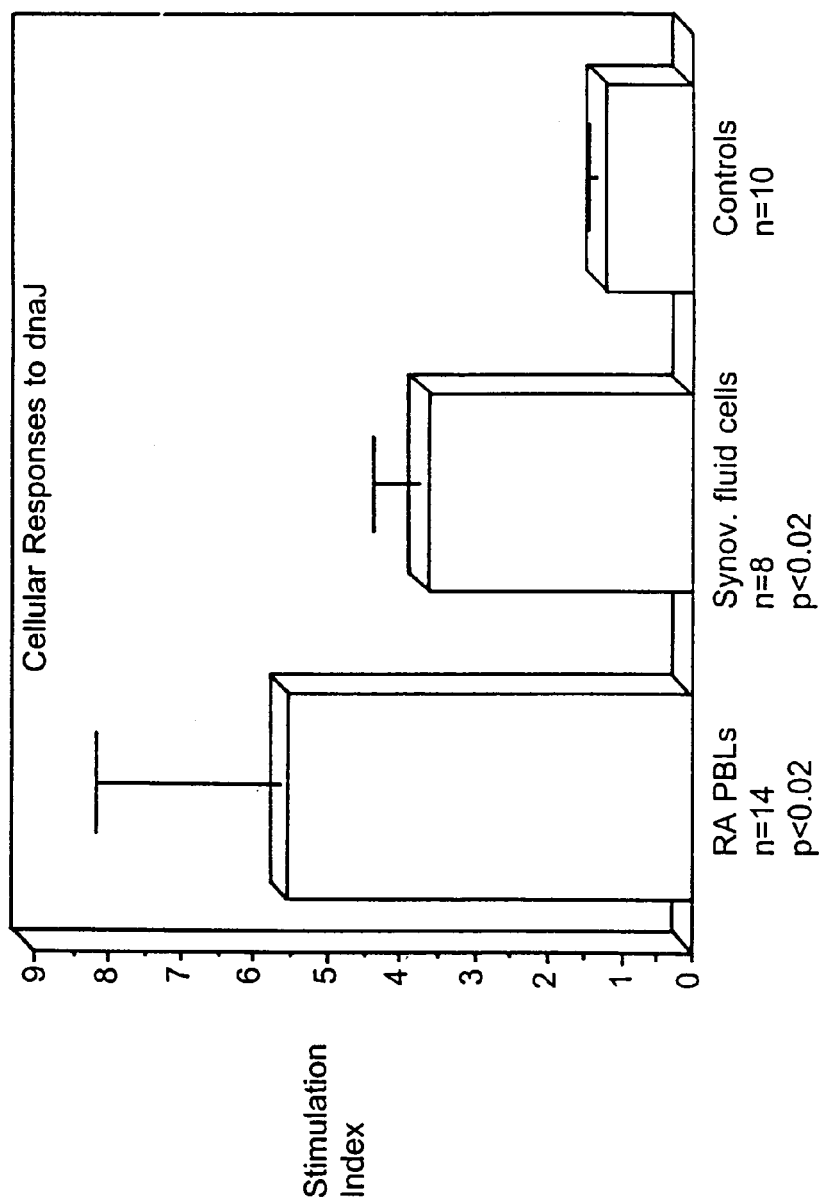
FIG. 1 quantifies proliferation of cultured lymphocytes from 22 patients with early, untreated RA ("early stage" RA) following exposure of the cells to intact bacterial dnaJ protein. The responses shown by bars in the graph of FIG. 1 are expressed in terms of a lymphocyte stimulation index; i.e., (CPM detected in cultures with dnaJ)/(CPM detected in cultures without dnaJ). "CPM" refers to counts-per-minute. The control culture tested consisted of lymphocytes obtained from humans without RA.

Based on cellular proliferation responses of PBL's from 14 early stage RA patients, and of synovial fluid lymphocytes from 8 early stage RA, the proliferation responses of the PBL's was approximately 3.6 times greater than the response of control subject lymphocytes while the response of synovial fluid lymphocytes was approximately 2.3 times greater than the response of control subject lymphocytes (see, FIG. 1).

EXAMPLE III

Response of Lymphocytes from Patients with Early Stage RA to RA Susceptibility Sequence Peptides Lymphocytes from patients with early stage RA were contacted with one of two RA susceptibility sequence peptides according to the protocol described in Example II. The peptides used were either a 15 amino acid synthetic peptide having the wild-type sequence QKRAAYDQYGHAAFE (SEQ ID NO: 4) or a 15 amino acid synthetic mutant peptide having the sequence DERAAYDQYGHAAFE (SEQ ID NO: 5).

As shown in FIG. 2, gauging the results according to the same standard of measurement used for Example II, the responses of PBL's to the wild-type peptide were more than 5 times greater than the responses of PBL's to the mutant peptide and approximately 9 times greater than the response of lymphocytes from control subjects to the wild-type peptide.

EXAMPLE IV

Inhibition of Antibody Binding to dnaJ

Microtiter plates were coated with recombinant dnaJ (10 μg/ml). Either sera obtained from patients with early stage RA or sera from control subjects were diluted 1:100 in borate buffered saline. Half of each specimen was incubated overnight at 4° C. with the wild-type dnaJ peptide described in Example III. Then the paired serum specimens were added to the dnaJ coated plates.

After 4 hours incubation, antibody binding was detected with alkaline phosphatase labelled goat anti-human IgG; levels of detected antibody binding were determined according to the following formula:

$$\% \text{ inhibition} = 100 \frac{(1 - OD_{460} \text{with wild} - \text{type peptide})}{(OD_{460} \text{without wild} - \text{type peptide})}$$

As shown in FIG. 3, antibody binding to rdnaJ was inhibited to, by the wild-type RA susceptibility sequence peptide, approximately a 3 times greater extent in the RA sera than the inhibition detected in the control sera.

EXAMPLE V

Determination of Genetic Predisposition to RA by Immunoassay

Antibody responses to rdnaJ were measured by ELISA. 100 μl aliquots of $^r$dnaJ (10 μg/ml) or membrane proteins from HLA DR or DR41 homozygous cells (100 μg/ml) were used to coat ELISA plates at 4° C. overnight. Then different dilutions of rabbit sera were added for a 2 hour incubation at room temperature. After washing with BBS/0.2% Tween-20, bound antibody was detected by using alkaline phosphatase-conjugated goat anti-rabbit IgG (Boehringer-Mannheim Biochemicals) diluted 1:1000. The results are expressed in FIG. 4 as the mean OD at 405 nm of duplicate wells.

SUMMARY OF SEQUENCES

SEQ ID NO:1 is the open reading frame of the polynucleotide encoding E. coli K12 dnaJ.
SEQ ID NO:2 is the amino acid sequence of a RA susceptibility sequence variant.
SEQ ID NO:3 is the amino acid sequence of a RA susceptibility sequence variant.
SEQ ID NO:4 is the amino acid sequence for the bacterial dnaJp1 peptide.
SEQ ID NO:5 is the amino acid sequence for the bacterial dnaJpV peptide.
SEQ.ID.No:6 is the amino acid sequence for the bacterial dnaJp2 peptide.
SEQ.ID.No:7 is the amino acid sequence for the synthetic human S1 HLA peptide.
SEQ.ID.No:8 is the amino acid sequence for the synthetic human S2 HLA peptide.

What is claimed is:

1. An isolated polynucleotide which encodes bacterial dnaJp1 peptide having the amino acid sequence of SEQ ID NO: 4.

2. The polynucleotide of claim 1, wherein the encoded DNAJp1 peptide is derived from a naturally occurring dnaJp protein that is encoded in the genome of a bacteria selected from at least on of the genera consisting of *Escherichia*, *Lactococcus* and *Proteus*.

3. A recombinant gene expression vector containing the polynucleotide of claim 1.

4. The polynucleotide of claim 3, wherein the recombinant gene expression vector further encodes at least one dnaJ polypeptide other than dnaJp1 peptide.

5. The polynucleotide of claim 4, wherein the dnaJ polypeptide is found in a human dnaJ protein.

* * * * *